US011110240B2

(12) United States Patent
Hacker et al.

(10) Patent No.: US 11,110,240 B2
(45) Date of Patent: Sep. 7, 2021

(54) ENDOTRACHEAL TUBE WITH TUBE COATING

(71) Applicant: Medtronic Xomed, Inc., Jacksonville, FL (US)

(72) Inventors: David C. Hacker, Jacksonville, FL (US); Wenjeng Li, Saint Johns, FL (US); Matthew L. Cantwell, Orange Park, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 820 days.

(21) Appl. No.: 15/697,762

(22) Filed: Sep. 7, 2017

(65) Prior Publication Data

US 2019/0070375 A1    Mar. 7, 2019

(51) Int. Cl.
*A61M 16/04* (2006.01)
*A61B 1/267* (2006.01)
*A61N 1/05* (2006.01)
*A61B 5/296* (2021.01)
(Continued)

(52) U.S. Cl.
CPC ........... *A61M 16/04* (2013.01); *A61B 1/2673* (2013.01); *A61B 5/296* (2021.01); *A61B 5/316* (2021.01); *A61B 5/394* (2021.01); *A61N 1/0517* (2013.01); *A61M 16/0434* (2013.01); *A61M 2205/0233* (2013.01); *A61M 2230/60* (2013.01); *A61N 1/0519* (2013.01)

(58) Field of Classification Search
CPC .............. A61M 16/04; A61M 16/0434; A61M 2205/0233; A61M 2230/60; A61B 1/2673; A61B 5/04012; A61B 5/04886; A61B 5/0492; A61B 2017/00853; A61N 1/0517; A61N 1/0519
See application file for complete search history.

(56) References Cited

U.S. PATENT DOCUMENTS

| 1,864,688 A | 6/1932 | Frank |
| 2,107,835 A | 2/1938 | Pierce |
| 2,429,585 A | 10/1947 | Rogoff |

(Continued)

FOREIGN PATENT DOCUMENTS

| CN | 2056003 | 4/1990 |
| CN | 2232257 | 8/1996 |

(Continued)

OTHER PUBLICATIONS

Restriction Requirement for U.S. Appl. No. 15/682,767 dated May 1, 2018 (5 pages).

(Continued)

*Primary Examiner* — Eun Hwa Kim
*Assistant Examiner* — Adam Z Minchella
(74) *Attorney, Agent, or Firm* — Dicke, Billig & Czaja, PLLC (57) ABSTRACT

An apparatus for monitoring EMG signals of a patient's laryngeal muscles includes an endotracheal tube having an exterior surface, and a tube coating applied to the exterior surface via spraying of a homogeneous solution onto the endotracheal tube or immersion of the endotracheal tube in the homogeneous solution. A conductive electrode is formed on the tube coating. The conductive electrode is configured to receive the EMG signals from the laryngeal muscles.

20 Claims, 4 Drawing Sheets

(51) Int. Cl.
    *A61B 5/316*    (2021.01)
    *A61B 5/394*    (2021.01)

(56) References Cited

U.S. PATENT DOCUMENTS

| | | | |
|---|---|---|---|
| 2,618,684 A | 11/1952 | Bergan | |
| 2,872,505 A | 2/1959 | Ustin | |
| 3,165,575 A | 1/1965 | Lynch, Jr. et al. | |
| 3,494,364 A | 2/1970 | Peters | |
| 3,528,050 A | 9/1970 | Hindenburg | |
| 3,734,094 A | 5/1973 | Calinog | |
| 3,783,178 A | 1/1974 | Philibert et al. | |
| 3,892,455 A | 7/1975 | Sotolongo | |
| 3,951,136 A | 4/1976 | Wall | |
| 4,090,518 A | 5/1978 | Elam | |
| 4,176,660 A | 12/1979 | Mylrea et al. | |
| 4,231,365 A | 11/1980 | Scarberry | |
| 4,304,239 A | 12/1981 | Perlin | |
| 4,349,031 A | 9/1982 | Perlin | |
| 4,369,794 A | 1/1983 | Furler | |
| 4,461,304 A | 7/1984 | Kuperstein | |
| 4,647,713 A | 3/1987 | de Nijis et al. | |
| 4,776,808 A | 10/1988 | Davidson | |
| 4,836,214 A | 6/1989 | Sramek | |
| 4,863,390 A | 9/1989 | Cera et al. | |
| 4,890,623 A | 1/1990 | Cook et al. | |
| 4,906,244 A | 3/1990 | Pinchuk et al. | |
| 4,960,133 A | 10/1990 | Hewson | |
| 4,967,759 A | 11/1990 | Teves | |
| 5,024,228 A | 6/1991 | Goldstone et al. | |
| 5,096,445 A | 3/1992 | Lostumo | |
| 5,103,817 A * | 4/1992 | Reisdorf | A61M 16/0436 128/207.15 |
| 5,125,406 A | 6/1992 | Goldstone et al. | |
| 5,135,001 A | 8/1992 | Sinofsky et al. | |
| 5,170,803 A | 12/1992 | Hewson et al. | |
| 5,286,211 A | 2/1994 | McIntosh | |
| 5,364,281 A | 11/1994 | Leto | |
| 5,379,765 A | 1/1995 | Kajiwara et al. | |
| 5,429,617 A | 7/1995 | Hammersmark | |
| 5,464,404 A | 11/1995 | Abela et al. | |
| 5,554,176 A | 9/1996 | Maddison et al. | |
| 5,584,290 A | 12/1996 | Brain | |
| 5,672,065 A | 9/1997 | Womack | |
| 5,782,744 A | 7/1998 | Money | |
| 5,782,774 A | 7/1998 | Shmulewitz | |
| 5,785,051 A | 7/1998 | Lipscher et al. | |
| 5,836,874 A | 11/1998 | Swanson et al. | |
| 5,864,093 A | 1/1999 | Hecock et al. | |
| 5,911,585 A | 6/1999 | Zwit | |
| 5,924,984 A | 7/1999 | Rao | |
| 5,972,026 A | 10/1999 | Laufer et al. | |
| 6,010,500 A | 1/2000 | Sherman et al. | |
| 6,032,065 A | 2/2000 | Brown | |
| 6,062,223 A | 5/2000 | Palazzo et al. | |
| 6,082,175 A | 7/2000 | Yoshikawa et al. | |
| 6,095,987 A | 8/2000 | Shmulewitz et al. | |
| 6,142,993 A | 11/2000 | Whayne et al. | |
| 6,148,222 A | 11/2000 | Ramsey, III | |
| 6,226,548 B1 | 5/2001 | Foley et al. | |
| 6,259,938 B1 | 7/2001 | Zarychta et al. | |
| 6,266,548 B1 | 7/2001 | Lamade et al. | |
| 6,266,549 B1 | 7/2001 | Melnikoff et al. | |
| 6,292,701 B1 | 9/2001 | Prass et al. | |
| 6,334,068 B1 | 12/2001 | Hacker | |
| 6,343,233 B1 | 1/2002 | Werner et al. | |
| 6,357,447 B1 | 3/2002 | Swanson et al. | |
| 6,398,596 B1 | 6/2002 | Malin | |
| 6,443,156 B1 | 9/2002 | Niklason et al. | |
| 6,463,327 B1 | 10/2002 | Lurie et al. | |
| 6,547,788 B1 | 4/2003 | Maguire et al. | |
| 6,584,347 B1 | 6/2003 | Sinderby | |
| 6,626,841 B1 | 9/2003 | Atlee, III | |
| 6,626,899 B2 | 9/2003 | Houser et al. | |
| 6,654,634 B1 | 11/2003 | Prass | |
| 6,735,471 B2 | 5/2004 | Hill et al. | |
| 6,869,431 B2 | 3/2005 | Maguire et al. | |
| 6,877,512 B2 | 4/2005 | Imai et al. | |
| 6,976,857 B1 | 12/2005 | Shukla | |
| 7,008,419 B2 | 3/2006 | Shadduck | |
| 7,146,222 B2 | 12/2006 | Boling | |
| 7,153,146 B2 | 12/2006 | Shimizu et al. | |
| 7,179,345 B2 | 2/2007 | Shkolnik | |
| 7,216,001 B2 | 5/2007 | Hacker et al. | |
| 7,293,562 B2 | 11/2007 | Malecki et al. | |
| 7,507,239 B2 | 3/2009 | Shadduck | |
| 7,583,991 B2 | 9/2009 | Rea | |
| 7,736,362 B2 | 6/2010 | Eberl et al. | |
| 7,794,256 B1 | 9/2010 | Sochor | |
| 7,972,308 B2 | 7/2011 | Putz | |
| 8,145,289 B2 | 3/2012 | Calabro' et al. | |
| 8,152,803 B2 | 4/2012 | Edwards et al. | |
| 8,224,422 B2 | 7/2012 | Mottola et al. | |
| 8,352,012 B2 | 1/2013 | Besio | |
| 8,467,844 B2 | 6/2013 | Rea et al. | |
| 8,634,894 B2 * | 1/2014 | Rea | A61M 16/04 600/380 |
| 8,688,237 B2 | 4/2014 | Stanislaus et al. | |
| 8,886,280 B2 | 11/2014 | Kartush | |
| 9,037,226 B2 | 5/2015 | Hacker et al. | |
| 9,060,744 B2 | 6/2015 | Li | |
| 9,289,141 B2 | 3/2016 | Lowery et al. | |
| 9,398,865 B2 | 7/2016 | Li | |
| 9,763,624 B2 | 9/2017 | Stanislaus et al. | |
| 9,907,484 B2 | 3/2018 | Li | |
| 9,913,594 B2 | 3/2018 | Li et al. | |
| 9,918,675 B2 | 3/2018 | Hacker et al. | |
| 9,918,676 B2 | 3/2018 | Hacker | |
| 9,931,079 B2 | 4/2018 | Li et al. | |
| 10,092,240 B2 | 10/2018 | Hacker | |
| 2001/0018281 A1 | 8/2001 | Royer | |
| 2002/0016615 A1 | 2/2002 | Dev et al. | |
| 2002/0032468 A1 | 3/2002 | Hill et al. | |
| 2002/0188332 A1 | 12/2002 | Lurie et al. | |
| 2003/0018327 A1 | 1/2003 | Truckai et al. | |
| 2003/0074039 A1 | 4/2003 | Puskas | |
| 2003/0215564 A1 * | 11/2003 | Heller | B05D 1/005 427/2.25 |
| 2004/0121146 A1 * | 6/2004 | He | C23C 14/0036 428/332 |
| 2004/0186461 A1 | 9/2004 | DiMatteo | |
| 2004/0230110 A1 | 11/2004 | Sinderby et al. | |
| 2005/0085111 A1 | 4/2005 | Clark et al. | |
| 2005/0113686 A1 | 5/2005 | Peckham | |
| 2005/0159659 A1 | 7/2005 | Sawan et al. | |
| 2005/0222656 A1 | 10/2005 | Wahlstrand et al. | |
| 2005/0255727 A1 | 11/2005 | Alladice | |
| 2006/0012671 A1 | 1/2006 | Nimri et al. | |
| 2006/0025702 A1 | 2/2006 | Sterrantino et al. | |
| 2006/0116564 A1 | 6/2006 | Mintchev et al. | |
| 2006/0241725 A1 | 10/2006 | Libbus et al. | |
| 2006/0254595 A1 | 11/2006 | Rea | |
| 2007/0074728 A1 | 4/2007 | Rea | |
| 2007/0137651 A1 | 6/2007 | Glassenberg et al. | |
| 2007/0142888 A1 | 6/2007 | Chavez | |
| 2007/0156041 A1 | 7/2007 | Rea | |
| 2007/0170928 A1 | 7/2007 | Fedan et al. | |
| 2007/0219551 A1 | 9/2007 | Honour et al. | |
| 2008/0077043 A1 | 3/2008 | Malbrain et al. | |
| 2008/0140052 A1 | 6/2008 | Moller et al. | |
| 2008/0177190 A1 | 7/2008 | Libbus et al. | |
| 2008/0249507 A1 | 10/2008 | Hadani | |
| 2008/0255441 A1 | 10/2008 | Hadani | |
| 2008/0300650 A1 | 12/2008 | Gerber et al. | |
| 2009/0227885 A1 | 9/2009 | Lowery et al. | |
| 2010/0006103 A1 | 1/2010 | McGinnis et al. | |
| 2010/0036229 A1 | 2/2010 | Weekamp et al. | |
| 2010/0063376 A1 | 3/2010 | Kartush | |
| 2010/0074932 A1 * | 3/2010 | Talsma | A61K 33/30 424/409 |
| 2010/0087782 A1 | 4/2010 | Ghaffari et al. | |
| 2010/0145178 A1 * | 6/2010 | Kartush | A61B 5/4893 600/380 |
| 2010/0168561 A1 | 7/2010 | Anderson | |

(56) References Cited

U.S. PATENT DOCUMENTS

| | | | |
|---|---|---|---|
| 2010/0168743 A1 | 7/2010 | Stone et al. | |
| 2010/0179417 A1 | 7/2010 | Russo | |
| 2010/0191311 A1 | 7/2010 | Scheiner | |
| 2010/0198099 A1 | 8/2010 | Murphy et al. | |
| 2010/0317956 A1 | 12/2010 | Kartush | |
| 2011/0023889 A1 | 2/2011 | Lin et al. | |
| 2011/0030694 A1 | 2/2011 | Schaner et al. | |
| 2011/0071379 A1 | 3/2011 | Rea et al. | |
| 2011/0190596 A1 | 8/2011 | Hacker et al. | |
| 2011/0230734 A1 | 9/2011 | Fain et al. | |
| 2011/0245647 A1 | 10/2011 | Stanislaus et al. | |
| 2011/0301587 A1 | 12/2011 | Deem et al. | |
| 2011/0306861 A1 | 12/2011 | Thramann et al. | |
| 2012/0016256 A1 | 1/2012 | Mabary et al. | |
| 2012/0024292 A1 | 2/2012 | Sandmore et al. | |
| 2012/0055257 A1 | 3/2012 | Shaw-Klein | |
| 2013/0150689 A1* | 6/2013 | Shaw-Klein | A61B 5/6821 600/345 |
| 2013/0172714 A1 | 7/2013 | Li et al. | |
| 2013/0251897 A1* | 9/2013 | Uang | B05D 7/04 427/157 |
| 2014/0148672 A1 | 5/2014 | Li | |
| 2014/0155720 A1 | 6/2014 | Stanislaus et al. | |
| 2014/0275914 A1* | 9/2014 | Li | A61B 5/04886 600/373 |
| 2015/0250423 A1 | 9/2015 | Hacker et al. | |
| 2015/0275026 A1* | 10/2015 | Jennings | A61L 29/085 514/152 |
| 2016/0038072 A1 | 2/2016 | Brown et al. | |
| 2016/0038073 A1 | 2/2016 | Brown et al. | |
| 2016/0038074 A1 | 2/2016 | Brown et al. | |
| 2016/0198720 A1* | 7/2016 | Yoshida | A01N 59/00 424/613 |
| 2016/0262699 A1 | 9/2016 | Goldstone et al. | |
| 2016/0287112 A1 | 10/2016 | McFarlin et al. | |
| 2016/0287861 A1 | 10/2016 | McFarlin et al. | |
| 2016/0324475 A1 | 11/2016 | Hacker | |
| 2016/0345905 A1 | 12/2016 | Li | |
| 2017/0007146 A1 | 1/2017 | Schulhauser et al. | |
| 2019/0381274 A1* | 12/2019 | Olson | A61B 5/287 |

FOREIGN PATENT DOCUMENTS

| | | |
|---|---|---|
| CN | 2827273 | 10/2006 |
| CN | 102781510 A1 | 11/2012 |
| DE | 29715344 | 1/1988 |
| DE | 19750705 | 3/2000 |
| EP | 0438863 | 11/1990 |
| EP | 1750368 A1 | 2/2007 |
| EP | 1782727 | 5/2007 |
| GB | 1214718 | 12/1970 |
| JP | H03-182230 | 8/1991 |
| JP | 2001-224554 | 8/2001 |
| JP | 2003-019200 | 1/2003 |
| JP | 2003-527164 | 9/2003 |
| JP | 2006-528890 | 12/2006 |
| JP | 2007-307185 | 11/2007 |
| JP | 2007-532152 | 11/2007 |
| JP | 2009-519763 | 5/2009 |
| JP | 2009-524482 | 7/2009 |
| KR | 1020060031799 | 4/2006 |
| WO | 199723163 | 7/1997 |
| WO | 200141638 | 6/2001 |
| WO | 2004/100786 | 11/2004 |
| WO | 2005/097246 | 10/2005 |
| WO | 2006012671 | 2/2006 |
| WO | 2006012672 | 2/2006 |
| WO | 2007/078827 | 7/2007 |
| WO | 2007/089491 | 8/2007 |
| WO | 2008/091928 | 7/2008 |
| WO | 2011/041690 | 4/2011 |
| WO | 2013/008106 | 1/2013 |
| WO | 2013008106 A1 | 1/2013 |
| WO | 2015080721 A1 | 6/2015 |

OTHER PUBLICATIONS

Non-Final Office Action for U.S. Appl. No. 15/682,767 dated Aug. 29, 2018 (59 pages).
Notice of Allowance for U.S. Appl. No. 15/899,441 dated Jun. 6, 2018 (8 pages).
Canada 1st Examiner's Report for 2860422 dated May 28, 2018 (4 pages).
Chinese 1st Office Action for 201380071314.4 dated Aug. 23, 2018 (17 pages).
International Search Report and Written Opinion, PCT/US2018/049713, dated Nov. 22, 2018 (16 pages).
Notice of Allowance for U.S. Appl. No. 14/175,165 dated May 22, 2017 (12 pages).
U.S. Appl. No. 15/217,572, filed Jul. 22, 2016, Inventor: David C. Hacker (65 pages).
Non-Final Office Action for U.S. Appl. No. 15/217,572 dated Feb. 9, 2017 (13 pages).
Final Office Action for U.S. Appl. No. 15/217,572 dated Jun. 6, 2017 (22 pages).
Non-Final Office Action for U.S. Appl. No. 13/343,283, dated Oct. 2, 2014 (26 pages).
Final Office Action for U.S. Appl. No. 13/343,283, dated May 26, 2015 (18 pages).
Advisory Action for U.S. Appl. No. 13/343,283, dated Aug. 28, 2015 (4 pages).
Non-Final Office Action for U.S. Appl. No. 13/343,283, dated Jan. 13, 2016 (19 pages).
Final Office Action for U.S. Appl. No. 13/343,283 dated Jul. 15, 2016 (22 pages).
Advisory Action for U.S. Appl. No. 13/343,283 dated Sep. 26, 2016 (4 pages).
Office Action for U.S. Appl. No. 13/343,283 dated Jan. 6, 2017 (24 pages).
Electric Motion Company, webpage "Telephony & CATV Products [Bronze Vise Type Connectors]" published Aug. 19, 2007, retrieved via Wayback Machine Jun. 20, 2016 (11 pages).
Southern Grounding Products, webpage "Grounding & ground Rod Clamps" published Nov. 19, 2008, retrieved via Wayback Machine Jun. 20, 2016 (5 pages).
Australian 1st Examination Report for 2012363699 dated Sep. 8, 2016 (3 pages). (.141).
Chinese 1st Office Action for 2012800710743 dated Oct. 30, 2015 (12 pages). (.231).
Japanese 1st Office Action for 2014-551252 dated Oct. 20, 2016 (3 pages). (.441).
Australian 2nd Examination Report for 2012363699 dated Jun. 22, 2017 (6 pages). (.141).
Non-Final Office Action for U.S. Appl. No. 13/688,818 dated Mar. 13, 2014 (10 pages).
Final Office Action for U.S. Appl. No. 13/688,818 dated Jun. 25, 2014 (10 pages).
Non-Final Office Action for U.S. Appl. No. 13/688,818 dated Oct. 9, 2014 (7 pages).
Notice of Allowance for U.S. Appl. No. 13/688,818 dated Feb. 20, 2015 (7 pages).
International Search Report and Written Opinion, PCT/US2013/072193, dated Mar. 11, 2014 (18 pages).
Australian 1st Examination Report for 2013406220 dated May 19, 2016 (3 pages). (.141).
Non-Final Office Action for U.S. Appl. No. 14/747,257 dated Nov. 17, 2015 (10 pages).
Notice of Allowance for U.S. Appl. No. 14/747,257 dated Mar. 23, 2016 (5 pages).
Final Office Action for U.S. Appl. No. 15/219,726 dated Oct. 21, 2016 (34 pages).
Advisory Action for U.S. Patent Appl. No. 15/219,726 dated Jan. 5, 2017 (4 pages).
Non-Final Office Action for U.S. Appl. No. 15/219,726 dated Apr. 11, 2017 (23 pages).
European Office Action for Application No. 14720826.8, dated Aug. 2, 2016 (8 pgs).

(56) References Cited

OTHER PUBLICATIONS

European Office Action for Application No. 14720826.8, dated Feb. 1, 2017 (6 pgs).
Defendants' Invalidity Contentions and Document Production Pursuant to Patent Local Rules 3-3 and 3-4; *Neurovision Medical Products, Inc. v. Medtronic Public Limited Company, Medtronic, Inc.; Medtronic Xomed, Inc. HCA Holdings, Inc.; and Healthtrust Purchasing Group, L.P.*; Civ. No. 2:16-cv-00127-JRP-RSP, signed by James M. Hilmert, date Jun. 10, 2016 (147 pages).
Hon, Li & Hutchings, "Direct writing technology—Advances and developments," CIRP Annals—Manufacturing Technology, vol. 57, Issue 2, presented on Aug. 25, 2008 and published Oct. 28, 2008, pp. 601-620 (20 pages).
Kartush et al., "Intraoperative Facial Nerve Monitoring," Ch. 5, Neuromonitoring in Otology and Head and Neck Surgery, Raven Press, Ltd., p. 99-120 (1992) (22 pages).
Goldstone A., Schettino R., "The Electrode Endotracheal Tube: A State of the Art Method for Monitoring the Recurrent Laryngeal Nerve-Vocal Cord Muscle Integrity in the Intubated Patient," presented to the American Academy of Otolaryngology/Head & Neck Surgery Annual National Meeting, San Diego, CA. (Sep. 1990) (1 page).
Eisele D.W., Goldstone A., "Electrophysiologic Identification and Preservation of the Superior Laryngeal Nerve During Thyroid Surgery," The Laryngescope, vol. 101, Issue 3, pp. 313-315 (Mar. 1991) (3 pages).
Bakhshaee et al., "Evaluation of the Distance Between Anterior Commissure of True Vocal Folds and the First Tracheal Ring and Related Laryngeal Indices in 40 Human Cadavers," J. Voice, vol. 30, No. 2, p. 159, col. 1 (2016) (3 pages).
Sprinzl et al., "Morphometric Measurements of the Cartilaginous Larynx: an Anatomic Correlate of Laryngeal Surgery," Head & Neck, Figs. 3-4, Tables 2-3, p. 743-750 (Dec. 1999) (8 pages).
Witt, Robert L., "Recurrent Laryngeal Nerve Electrophysiologic Monitoring in Thyroid Surgery: The Standard of Care?" J. Voice, vol. 19, No. 3, pp. 497-500 (2005) (4 pages).
Strauss, Christian et al., "Electrophysiological Localization of Motor Areas within the Rhomboid Fossa During Brainstem Surgery," ECoG, OAE and Intraoperative Monitoring: Proceedings of the First International Conference, (D. Höhmann, ed.) pp. 375-378 (Sep. 1992) (10 pages).
Møller, Aage R., "Monitoring and Mapping the Cranial Nerves and the Brainstem," Ch. 13, Neurophysiological in Neurosurgery: A Modern Intraoperative Approach, Academic Press, pp. 291-318 (2002) (36 pages).
Wang et al., "Prognostic Indicators of Unilateral Vocal Fold Paralysis," Archives of Otolaryngology Head Neck Surgery, vol. 134, No. 4, pp. 380-388 (Apr. 2008) (11 pages).
Dimopoulos et al., "Quantitative Estimation of the Recurrent Laryngeal Nerve Irritation by Employing Spontaneous Intraoperative Electromyographic Monitoring During Anterior Cervical Discectomy and Fusion," J. Spinal Disorder Tech, vol. 22, No. 1, pp. 1-7 (Feb. 2009) (7 pages).
Ajmani, M. L., "A Metrical Study of the Laryngeal Skeleton in Adult Nigerians," J. Anat., vol. 171, pp. 187-191 (1990) ("Ajmani Article") (5 pages).
Grillo, Hermes, Surgery of the Trachea and Bronchi, BC Decker Inc., pp. 39-59 (2004) (23 pages).
Livingstone, Churchill, Gray's Anatomy, pp. 1637-1657 (1995) (28 pages).
Special 510(k) Premarket Notification, K094054, Neurovision® EMG Endotracheal Tube dated May 14, 2010 (6 pages).
Pictures of a NuVasive EMG tube (5 pages). The first public use of the NuVasive EMG tube is unclear to Applicant. For purposes of Examination only, the NuVasive EMG tube may be considered to be prior art to the present application, although Applicant reserves the right to challenge this in any future proceeding. Applicant has submitted a physical sample of the NuVasive EMG tube in U.S. Appl. No. 15/217,572, filed Jul. 22, 2016.
David L. Bourell et al., Solid Freeform Fabrication Proceedings, Aug. 2004, © 2004 The University of Texas at Austin (15 pages).
ECOM™ Brochure for Endotracheal Cardiac Output Monitor, © 2008 ConMed Corporation Sep. 2008 (2 pages).
James K. Brown et al., Parasympathetic Innervation of the Cervical Trachealis Muscle in Living Dogs, © 1982 The American Physiology Society, vol. 53, No. 3, pp. 617-625 (9 pages).
NuVasive® NVJBB® EMG Endotracheal Tube IFU Product Insert (2 pages). We are not certain of its date, but for purposes of examination we request the examiner consider it as possible art. Applicant expressly reserves the right to contest the prior art date of this document should the Examiner find it relevant.
NuVasive® NeuroVision® EMG Endotracheal Tube brochure—© 2010 NuVasive, Inc. (4 pages).
Cahide Topsakal et al., Intraoperative Monitoring of Lower Cranial Nerves in Skull Base Surgery: Technical Report and Review of 123 Monitored Cases, Neurosurg. Rev., vol. 31, pp. 45-52 Published Online Oct. 24, 2007 © Springer-Verlag 2007 (9 pages).
Jasper R. Daube et al., Clinical Neurophysiology, Third Edition, Oxford University Press. Chapters 25, 43 and 44, © 2009 (71 pages).
U.S. Appl. No. 61/244,402, filed Sep. 21, 2009 (11 pages).
U.S. Appl. No. 14/945,167, filed Nov. 18, 2015 (89 pages).
U.S. Appl. No. 14/945,208, filed Nov. 18, 2015 (88 pages).
Affidavit of Christopher Butler with Exhibit A dated Nov. 10, 2016 (8 pages).
Decision-Institution of Inter Partes Review; *Medtronic Xomed, Inc. v. Neurovision Medical Products, Inc.*; PTAB Case IPR2016-01405; for U.S. Pat. No. 8,634,894 entered Dec. 29, 2016 (35 pages).
Petition for Inter Partes Review; *Medtronic Xomed, Inc. v. Neurovision Medical Products, Inc.*; PTAB Case IPR2017-00456; for U.S. Pat. No. 8,634,894 dated Dec. 9, 2016 (58 pages).
Patentee's Preliminary Response to Petition for Inter Partes Review; *Medtronic Xomed, Inc. v. Neurovision Medical Products, Inc.*; PTAB Case IPR2016-01405; for U.S. Pat. No. 8,634,894 dated Oct. 20, 2016 (74 pages).
Declaration of Mike Lieu—Exhibit 2002 to Patentee's Preliminary Response to Petition for Inter Partes Review dated Oct. 20, 2016 (7 pages).
Declaration of Stephen W. Blakely—Exhibit 2003 to Patentee's Preliminary Response to Petition for Inter Partes Review dated Oct. 20, 2016 (7 pages).
Declaration of James Lee Rea—Exhibit 2004 to Patentee's Preliminary Response to Petition for Inter Partes Review dated Oct. 20, 2016 (6 pages).
Declaration of Ryan M. Rea—Exhibit 2005 to Patentee's Preliminary Response to Petition for Inter Partes Review dated Oct. 20, 2016 (2 pages).
"Thyroid Surgery May Result in Paralysis of Vocal Cords," Wall Street Journal article dated Aug. 10, 2001 to Exhibit 2006 to Patentee's Preliminary Response to Petition for Inter Partes Review dated Oct. 20, 2016 (4 pages).
Medtronic webpage at http://medtronic.com/us-en/healthcare-nim-nerve-monitoring-systems/related-nerve-monitoring-products.html—Exhibit 2007 to Patentee's Preliminary Response to Petition for Inter Partes Review dated Oct. 20, 2016 (5 pages).
Medtronic product recall notice—Exhibit 2008 to Patentee's Preliminary Response to Petition for Inter Partes Review dated Oct. 20, 2016 (4 pages).
MicroPenning: How It Works—Exhibit 2009 to Patentee's Preliminary Response to Petition for Inter Partes Review dated Oct. 20, 2016 (2 pages).
MicroPenning: Overview—Exhibit 2010 to Patentee's Preliminary Response to Petition for Inter Partes Review dated Oct. 20, 2016 (3 pages).
U.S. Pat. No. 4,461,304 to Kuperstein—Exhibit 2011 to Patentee's Preliminary Response to Petition for Inter Partes Review dated Oct. 20, 2016 (10 pages).
U.S. Appl. No. 61/126,567—Exhibit 2012 to Patentee's Preliminary Response to Petition for Inter Partes Review dated Oct. 20, 2016 (8 pages).

(56) References Cited

OTHER PUBLICATIONS

NuVasive, Inc.'s Petition for Inter Partes Review file in IPR2015-00502—Exhibit 2014 to Patentee's Preliminary Response to Petition for Inter Partes Review dated Oct. 20, 2016 (63 pages).
PTAB's Decision dated Jul. 16, 2015 in IPR2015-00502—Exhibit 2015 to Patentee's Preliminary Response to Petition for Inter Partes Review dated Oct. 20, 2016 (31 pages).
Table of page cites and summary regarding Exhibit 2001—Exhibit 2016 to Patentee's Preliminary Response to Petition for Inter Partes Review dated Oct. 20, 2016 (14 pages).
Redacted Exhibit 2001—Confidential Neurovision emails regarding conception and reduction to practice—Exhibit 2017 to Patentee's Preliminary Response to Petition for Inter Partes Review dated Oct. 20, 2016 (140 pages).
Decision; *Medtronic Xomed, Inc.* v. *Neurovision Medical Products, Inc.*; PTAB Case IPR2016-01847; for U.S. Pat. No. 8,467,844 entered Mar. 23, 2017 (37 pages).
Korean Final Office Action for 10-2012-7011251 dated Jun. 28, 2017 (7 pages).
Final Office Action for U.S. Appl. No. 13/343,283 dated Jul. 11, 2017 (24 pages).
Japanese 1st Office Action for 2016-502632 dated Jul. 7, 2017 (8 pages).
Final Office Action for U.S. Appl. No. 15/219,726 dated Aug. 2, 2017 (10 pages).
Australian 1st Examination Report for Application No. 2014236572, dated Aug. 10, 2017 (4 pgs).
Non-Final Office Action for U.S. Appl. No. 13/826,323 dated Sep. 8, 2014 (9 pages).
Non-Final Office Action for U.S. Appl. No. 13/826,323 dated Dec. 15, 2014 (11 pages).
Final Office Action for U.S. Appl. No. 13/826,323 dated Mar. 23, 2015 (6 pages).
Advisory Action for U.S. Appl. No. 13/826,323 dated May 28, 2015 (3 pages).
Examiner's Answer for U.S. Appl. No. 13/826,323 dated Nov. 18, 2015 (6 pages).
Notice of Allowance for U.S. Appl. No. 13/826,323 dated Jun. 7, 2017 (5 pages).
Non Final Office Action for U.S. Appl. No. 15/692,738, dated Oct. 24, 2019 (71 pages).
International Search Report and Written Opinion, PCT/US2014/027810, dated Jul. 25, 2014 (18 pages).
"Applications of High-Pressure Balloons in the Medical Device Industry", 1999 Advanced Polymers, Inc. 1999, Mark A. Saab, President (19 pages).
Canadian 2nd Examiner's Report for 2775588 dated Sep. 5, 2017 (4 pages).
Notice of Allowance for U.S. Appl. No. 14/716,351 dated Sep. 27, 2017 (11 pages).
Advisory Action for U.S. Appl. No. 15/217,572 dated Sep. 29, 2017 (4 pages).
Notice of Allowance for U.S. Appl. No. 15/217,572 dated Nov. 3, 2017 (10 pages).
Notice of Allowance for U.S. Appl. No. 13/343,283 dated Oct. 12, 2017 (12 pages).
Corrected Notice of Allowability for U.S. Appl. No. 13/343,283 dated Nov. 1, 2017 (15 pages).
Australian 3rd Examination Report for 2012363699 dated Sep. 5, 2017 (3 pages).
European Office Action for Application No. 13812262.7, dated Aug. 2, 2017 (8 pages).
Notice of Allowance for U.S. Appl. No. 15/219,726 dated Oct. 2, 2017 (8 pages).
Notice of Allowance for U.S. Appl. No. 13/826,323 dated Sep. 12, 2017 (45 pages).
Notice of Allowance for U.S. Appl. No. 14/716,351 dated Jan. 22, 2018 (12 pages).
Notice of Allowance for U.S. Appl. No. 15/217,572 dated Jan. 22, 2018 (9 pages).
Notice of Allowance for U.S. Appl. No. 13/343,283 dated Jan. 19, 2018 (12 pages).
Notice of Allowance for U.S. Appl. No. 15/219,726 dated Dec. 20, 2017 (15 pages).
Notice of Allowance for U.S. Appl. No. 13/826,323 dated Dec. 19, 2017 (10 pages).
International Search Report and Written Opinion, PCT/US2012/069253, dated Feb. 28, 2013 (4 pages).
European Examination Report for Application No. 12818693.9 dated Oct. 25, 2017 (7 pages).
European Office Action for Application No. 14720826.8, dated Jul. 17, 2017 (6 pages).
European Examination Report for Application No. 14182496.1, dated Oct. 24, 2017 (5 pages).
Japanese Final (2nd) Office Action for 2016-502632 dated Feb. 21, 2018 (3 pages).
Restriction Requirement for U.S. Appl. No. 12/896,578 dated Jul. 24, 2012 (8 pages).
Non-Final Office Action for U.S. Appl. No. 12/896,578 dated Oct. 3, 2012 (16 pages).
Non-Final Office Action for U.S. Appl. No. 12/896,578 dated Sep. 19, 2013 (16 pages).
Notice of Allowance for U.S. Appl. No. 12/896,578 dated Feb. 27, 2014 (7 pages).
Notice of Allowance for U.S. Appl. No. 12/896,578 dated Jun. 9, 2014 (11 pages).
Notice of Allowance for U.S. Appl. No. 12/896,578 dated Aug. 5, 2014 (12 pages).
Notice of Allowance for U.S. Appl. No. 12/896,578 dated Oct. 6, 2014 (11 pages).
Notice of Allowance for U.S. Appl. No. 12/896,578 dated Jan. 28, 2015 (12 pages).
Notice of Allowance for U.S. Appl. No. 12/896,578 dated Mar. 30, 2015 (11 pages).
PCT Search Report dated Apr. 28, 2011 for PCT/US2010/051132 (17 pages).
International Preliminary Report on Patentability for PCT/US2010/051132, dated Dec. 5, 2011 (5 pages).
Australian Examination Report dated Feb. 25, 2013 (4 pages) re 2010300373.
Canadian 1st Examiner's Report for 2775588 dated Oct. 28, 2016 (4 pages). (.211).
Chinese 1st Office Action for 201080054559.2 dated Feb. 14, 2014 (5 pages).
Chinese 2nd Office Action for Application No. 201080054559.2, dated Jul. 17, 2014 (10 pages).
Japanese Office Action for Application No. 2012/532,355, dated Apr. 18, 2014 (7 pages).
European Examination Report for Application No. 10781544.1, dated Feb. 19, 2014 (4 pages). (.291).
Extended European Search Report for Serial No. 14182496.1, dated Nov. 28, 2014 (7 pages). (.292).
Korean 1st Office Action for 10-2012-7011251 dated Feb. 6, 2017 (13 pages).
Restriction Requirement for U.S. Appl. No. 14/716,351 dated Jan. 22, 2016 (5 pages).
Non-Final Office Action for U.S. Appl. No. 14/716,351 dated May 3, 2016 (25 pages).
Non-Final Office Action for U.S. Appl No. 14/716,351 dated Sep. 21, 2016 (6 pages).
Final Office Action for U.S. Appl. No. 14/716,351 dated Mar. 21, 2017 (30 pages).
Non-Final Office Action for U.S. Appl No. 14/716,351 dated May 17, 2017 (13 pages).
Non-Final Office Action for U.S. Appl. No. 12/896,593 dated Sep. 5, 2012 (17 pages).
Final Office Action for U.S. Appl. No. 12/896,593, dated Jan. 3, 2013 (13 pages).
Advisory Action for U.S. Appl. No. 12/896,593 dated Apr. 10, 2013 (7 pages).
Notice of Allowance for U.S. Appl. No. 12/896,593 dated Aug. 15, 2013 (11 pages).

(56) References Cited

OTHER PUBLICATIONS

Notice of Allowance for U.S. Appl. No. 12/896,593 dated Nov. 7, 2013 (13 pages).
PCT Search Report dated Feb. 4, 2011 for PCT/US2010/051145 (15 pages).
International Preliminary Report on Patentability dated Oct. 24, 2011 for PCT/US2010/051145 (12 pages).
Australian Examination Report No. 1 for Application No. 2010300379, dated May 30, 2014 (4 pages). (.141).
Australian Examination Report No. 1 for Application No. 2015200049, dated Mar. 10, 2016 (3 pages). (.142).
Canadian 1st Examiner's Report for 2776163 dated Oct. 28, 2016 (4 pages). (.211).
Chinese 1st Office Action for 201080054850.X dated Feb. 20, 2014 (19 pages).
Chinese 2nd Office Action for Application No. 201080054850.X, dated Jul. 23, 2014 (6 pages).
European Examination Report for Application No. 10779358.0, dated Feb. 19, 2014 (4 pages). (.291).
Extended European Search Report for Application No. 16176750.4, dated Nov. 22, 2016 (6 pages). (.292).
Japanese Office Action for Application No. 2012/532,356, dated Apr. 18, 2014 (7 pages).
Japanese Office Action for Application No. 2014/189873, dated Aug. 30, 2015 (5 pgs).
Notice of Allowance for U.S. Appl. No. 14/175,165 dated May 29, 2014 (28 pages).
Non-Final Office Action for U.S. Appl. No. 14/175,165, dated Aug. 15, 2014 (17 pages).
Final Office Action for U.S. Appl. No. 14/175,165, dated Dec. 4, 2014 (13 pages).
Non-Final Office Action for U.S. Appl. No. 14/175,165, dated Mar. 3, 2015 (12 pages).
Final Office Action for U.S. Appl. No. 14/175,165, dated Jun. 12, 2015 (16 pages).
Advisory Action for U.S. Appl. No. 14/175,165, dated Sep. 25, 2015 (6 pages).
Non-Final Office Action for U.S. Appl. No. 14/175,165 dated Jan. 5, 2016 (22 pages).
Final Office Action for U.S. Appl. No. 14/175,165 dated May 19, 2016 (24 pages).
Notice of Allowance for U.S. Appl. No. 14/175,165 dated Feb. 23, 2017 (13 pages).
Corrected Notice of Allowability for U.S. Appl. No. 14/175,165 dated Mar. 23, 2017 (18 pages).
India Examination Report for Application No. 847/MUMNP/2012, dated Feb. 26, 2019 (6 pages).
India Examination Report for Application No. 757/MUMNP/2012, dated Mar. 5, 2019 (8 pages).
Notice of Allowance for U.S. Appl. No. 15/682,767 dated Jan. 2, 2019 (10 pages).
Summons to Attend Oral Proceedings for Application No. 13812262.7, dated Nov. 5, 2018 (12 pages).
Canada 2nd Examiner's Report for 2860422 dated Mar. 19, 2019 (4 pages).
Canada Examiner's Report for 2,893,048 dated Jul. 2, 2020 (5 pages).

\* cited by examiner

```
┌─────────────────────────────────────────┐
│ ADD A SOLUTE TO A CONTAINER CONTAINING  │── 302
│         A MIXTURE OF SOLVENTS            │
└─────────────────────────────────────────┘
                    ↓
┌─────────────────────────────────────────┐
│  STIR THE COMBINATION OF THE SOLVENTS    │
│  AND THE SOLUTE WITH A MAGNETIC STIRRER  │── 304
│  UNTIL THE SOLUTE DISSOLVES TO FORM A    │
│         HOMOGENEOUS SOLUTION             │
└─────────────────────────────────────────┘
                    ↓
┌─────────────────────────────────────────┐
│  ADD A COLORANT TO THE SOLUTION TO FORM  │── 306
│           A COLORED SOLUTION             │
└─────────────────────────────────────────┘
                    ↓
┌─────────────────────────────────────────┐
│   CLEAN THE OUTER SURFACE OF THE EMG     │
│   ENDOTRACHEAL TUBE WITH ALCOHOL TO      │── 308
│          REMOVE ANY RESIDUE              │
└─────────────────────────────────────────┘
                    ↓
┌─────────────────────────────────────────┐
│  MASK REGIONS OF THE EMG ENDOTRACHEAL    │── 310
│     TUBE THAT ARE NOT TO BE COATED       │
└─────────────────────────────────────────┘
                    ↓
┌─────────────────────────────────────────┐
│   SPRAY THE COLORED SOLUTION ON THE EMG  │
│   ENDOTRACHEAL TUBE IN AN AEROSOL FORM   │
│   WHILE THE TUBE IS BEING ROTATED TO     │── 312
│   FORM A TUBE COATING ON UNMASKED        │
│   REGIONS OF THE OUTER SURFACE OF THE    │
│                 TUBE                     │
└─────────────────────────────────────────┘
                    ↓
┌─────────────────────────────────────────┐
│   FORM ELECTRODES ON AN OUTER SURFACE    │── 314
│           OF THE TUBE COATING            │
└─────────────────────────────────────────┘
                    ↓
┌─────────────────────────────────────────┐
│   PERFORM A BAKING PROCESS ON THE EMG    │
│   ENDOTRACHEAL TUBE WITH THE TUBE        │── 316
│   COATING AND ELECTRODES FORMED THEREON  │
└─────────────────────────────────────────┘
```

ENDOTRACHEAL TUBE WITH TUBE COATING

BACKGROUND

Endotracheal tubes include electrodes that are designed to snake contact with a patient's vocal cords to facilitate electromyographic (EMG) monitoring of the vocal cords during surgery when connected to an EMG monitoring device. Endotracheal tubes provide an open airway for patient ventilation, and provide for monitoring of EMG activity of the intrinsic laryngeal musculature when connected to an appropriate EMG monitor. Endotracheal tubes can provide continuous monitoring of the nerves supplying the laryngeal musculature during surgical procedures.

SUMMARY

One embodiment is directed to an apparatus for monitoring EMG signals of a patient's laryngeal muscles. The apparatus includes an endotracheal tube having an exterior surface, and a tube coating applied to the exterior surface via spraying of a homogeneous solution onto the endotracheal tube or immersion of the endotracheal tube in the homogeneous solution. A conductive electrode is formed on the tube coating. The conductive electrode is configured to receive the EMG signals from the laryngeal muscles.

DETAILED DESCRIPTION

Figure 1:
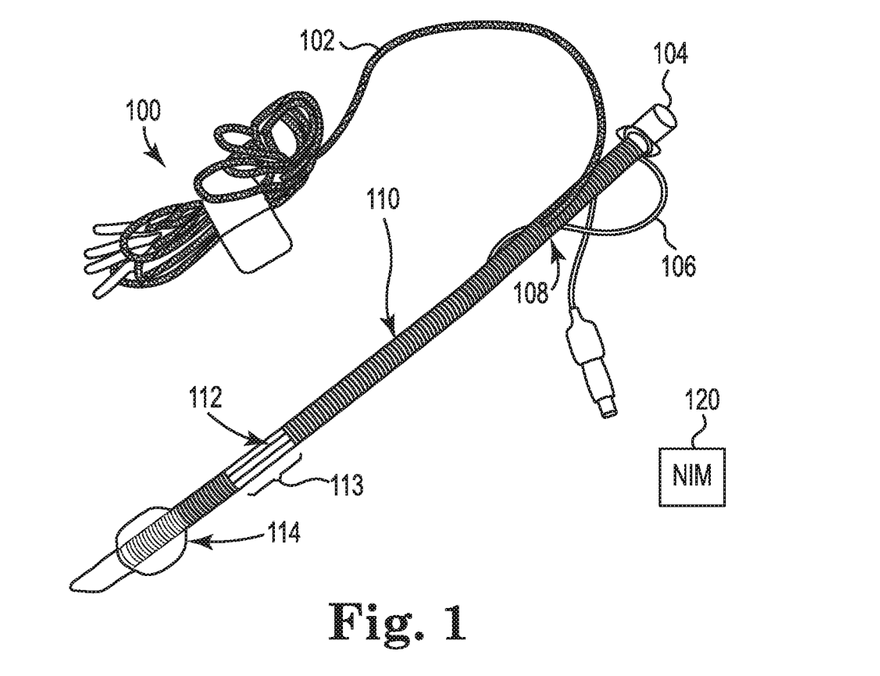
FIG. 1 is a diagram illustrating an EMG endotracheal tube apparatus with a tube coating according to one embodiment.
Figure 2:
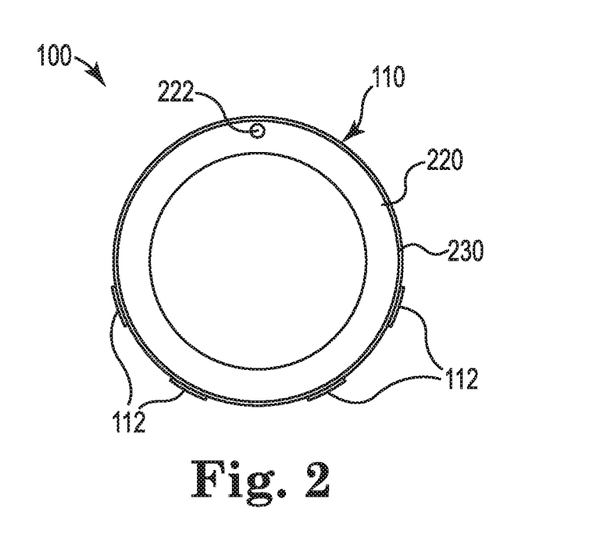
FIG. 2 is a diagram illustrating a cross-sectional view of the EMG endotracheal tube apparatus shown in FIG. 1 according to one embodiment.

FIG. 1 is a diagram illustrating an EMG endotracheal tube apparatus 100 with a tube coating according to one embodiment. FIG. 2 is a diagram illustrating a cross-sectional view of the EMG endotracheal tube apparatus 100 shown in FIG. 1 according to one embodiment. Endotracheal tube apparatus 100 includes solid wires 102, fitting 104, cuff inflating conduit 106, polymer endotracheal tube 110, electrodes 112, and cuff 114. In one embodiment, electrodes 112 are conductive ink electrodes that are printed on an electrode region 113 of the tube 110. Solid wires 102 are connected to electrodes 112 at interconnection 108.

Tube 110 transports gases to and from the lungs. Fitting 104 is configured to be connected to a respirating machine (not shown) for injecting air into the lungs and withdrawing air from the lungs. Cuff inflating conduit 106 is configured to be connected to a source of compressed air (not shown) for cuff 114. Cuff inflating conduit 106 communicates with a lumen 222 (FIG. 2) located in the wall 220 of tube 110, and the lumen communicates with cuff 114.

After endotracheal tube 110 is inserted into the trachea of a patient, electrodes 112 sense EMG signals, which are output to an EMG processing machine, such as nerve integrity monitor (NIM) device 120, via solid wires 102. Die cut tape may be used to tape tube 110 to a patient's mouth to secure the tube and keep it appropriately positioned.

As shown in FIG. 2, lumen 222 is located in the tube wall 220 of tube 110 for inflating the cuff 114 (FIG. 1). Tube coating 230 is formed on the outer surface of the tube wall 220. Conductive ink electrodes 112 are formed on the outer surface of the tube coating 230. In one embodiment, tube coating 230 is made from the following elements in the indicated proportions: 20 g polyvinyl chloride (PVC) pellets; 10 g cyclohexanone; 60 g tetrahydrofuran (THF); 30 g acetone; 60 g ink thinner; and trace amounts of food grade colorant. In one embodiment, the PVC pellets are dissolved in a mixture of solvents, including the cyclohexanone, THF, acetone, and ink thinner. The colorant is then added, and the resulting colored solution is sprayed on the tube 110 to form the tube coating 230. In some embodiments, the tube coating 230 has a coating thickness of about 10-100 microns.

The food grade colorant causes the tube 110 to have a color tint (e.g., a blue tint), with a transmittance of about 74-93%, as opposed to a clear tube with a transmittance of 100%. The transmittance may be varied by pigment, pigment concentration, and/or thickness of the tube coating 230. The color tint helps differentiate the coated tube from other EMG tubes, while still maintaining a high transmittance, which can be important for a monitoring tube. Different color tints may also be used to indicate different EMG tube sizes.

In some embodiments, tube coating 230 is only formed on the electrode region 113 (FIG. 1) of the tube 110, and the remainder of the external surface of the tube 110 is not covered by tube coating 230. In other embodiments, tube coating 230 is formed on the entire outer surface of the tube 110, or substantially the entire outer surface of the tube 110 (e.g., 90 percent or more of the outer surface area of the tube 110).

In one embodiment, conductive ink electrodes 112 are formed by tracing or printing a silver filled polymer conductive ink on tube coating 230. Conductive inks are available in variety of flowable material choices such as Silver, Carbon, Gold, Platinum, Palladium, Silver-Tungsten, and Silver-Titanium. Conductive inks can be deposited on the coating 230 using various known technologies such as PAD printing, screen printing, ink jet dispensing, digital printing, Micropen dispensing, painting, vapor deposition, and plasma sputtering. Conductive inks can be used both for stimulation and recording purposes in nerve monitoring applications.

EMG endotracheal tubes may have some surface contamination that adversely affects the adhesion of electrodes to the tubes. Forming the electrodes 112 on the tube coating 230, rather than directly on the outer surface of the tube 110 provides several advantages, including improved adhesion, flexibility, resistance to cracking, and improved shelf life.

Figure 3:
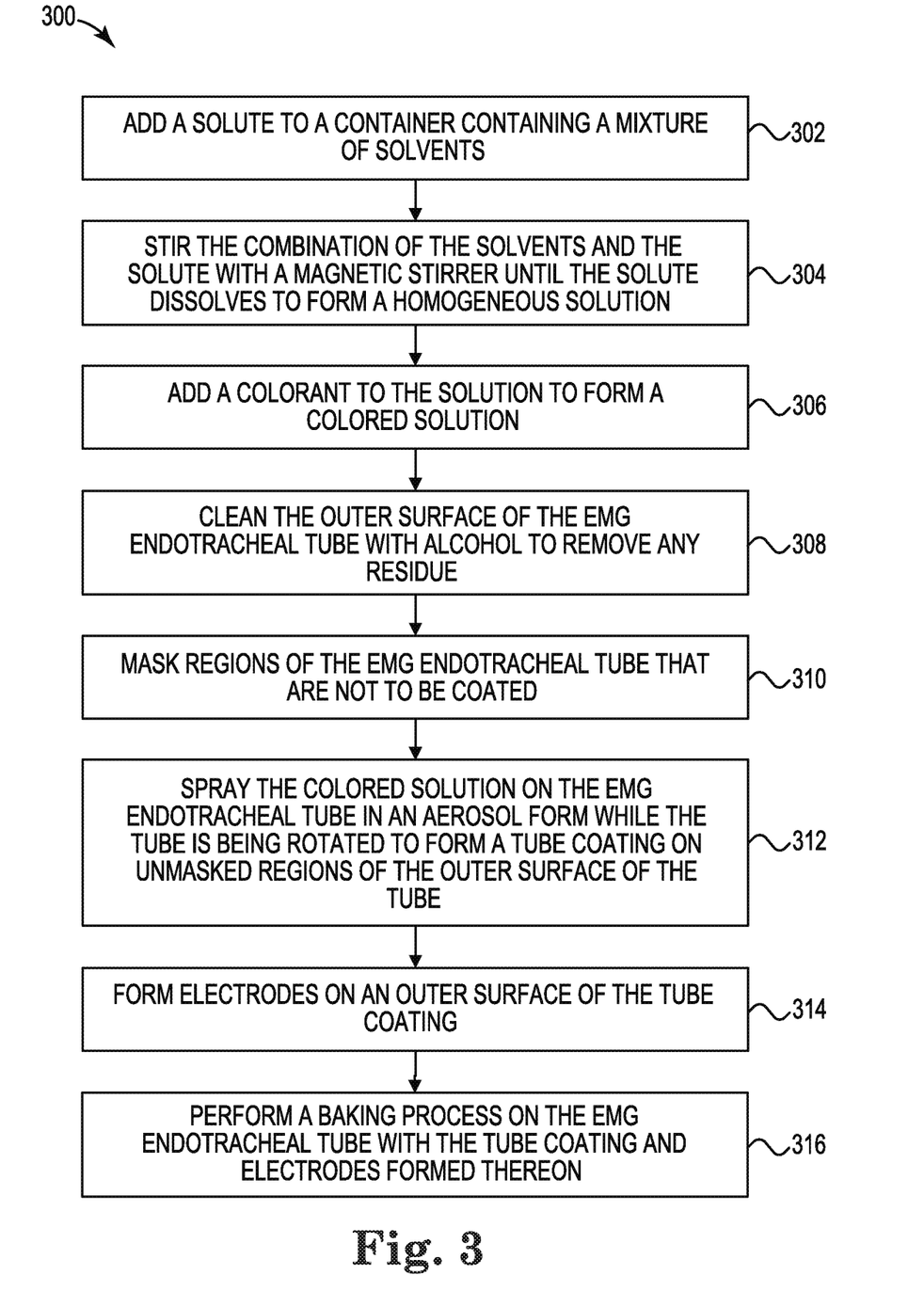
FIG. 3 is a flow diagram illustrating a method of applying electrodes to an EMG endotracheal tube according to one embodiment.

FIG. 3 is a flow diagram illustrating a method 300 of applying electrodes to an EMG endotracheal tube according to one embodiment. At 302 in method 300, a solute is added to a container containing a mixture of solvents. In some embodiments, the solute comprises PVC pellets, and the solvents include cyclohexanone, THF, acetone, and ink thinner. At 304, the combination of the solvents and the solute is stirred or mixed with a magnetic stirrer until the solute dissolves to form a homogeneous solution. At 306, a colorant is added to the solution to form a colored solution.

At 308 in method 300, the outer surface of the EMG endotracheal tube is cleaned with alcohol to remove any residue. At 310, regions of the EMG endotracheal tube that are not to be coated are masked. At 312, the colored solution is sprayed on the EMG endotracheal tube in an aerosol form while the tube is being rotated to form a tube coating on unmasked regions of the outer surface of the tube. At 314, electrodes are formed on an outer surface of the tube coating. In one embodiment, the electrodes are formed from a silver conductive ink, and are printed on the outer surface of the tube coating at 314.

At 316, the EMG endotracheal tube with the tube coating and electrodes formed thereon goes through a baking process. In one embodiment, the tube coating is allowed to air dry, rather than being baked, before formation of the electrodes at 314, so the method 300 involves only a single baking process (i.e., after formation of the electrodes).

In other embodiments, rather than spraying the colored homogeneous solution onto the EMG endotracheal tube, the tube is instead immersed in a bath of the colored homogeneous solution to form the tube coating.

One embodiment is directed to an apparatus for monitoring EMG signals of a patient's laryngeal muscles. The apparatus includes an endotracheal tube having an exterior surface, and a tube coating applied to the exterior surface via spraying of a homogeneous solution onto the endotracheal tube or immersion of the endotracheal tube in the homogeneous solution. A conductive electrode is formed on the tube coating. The conductive electrode is configured to receive the EMG signals from the laryngeal muscles.

The tube coating of the apparatus may cause the endotracheal tube to have a color tint. In one embodiment, the tube coating has a transmittance of about 74-93%. The tube coating may be applied only to an electrode region of the endotracheal tube. The tube coating may be formed from spraying the homogeneous solution in an aerosol form onto the endotracheal tube. The tube coating may be formed from PVC pellets dissolved in a mixture of solvents to form the homogeneous solution. The mixture of solvents may include cyclohexanone, tetrahydrofuran (THF), and acetone. The mixture of solvents may further include an ink thinner. The homogeneous solution may include a food grade colorant.

Figure 4:
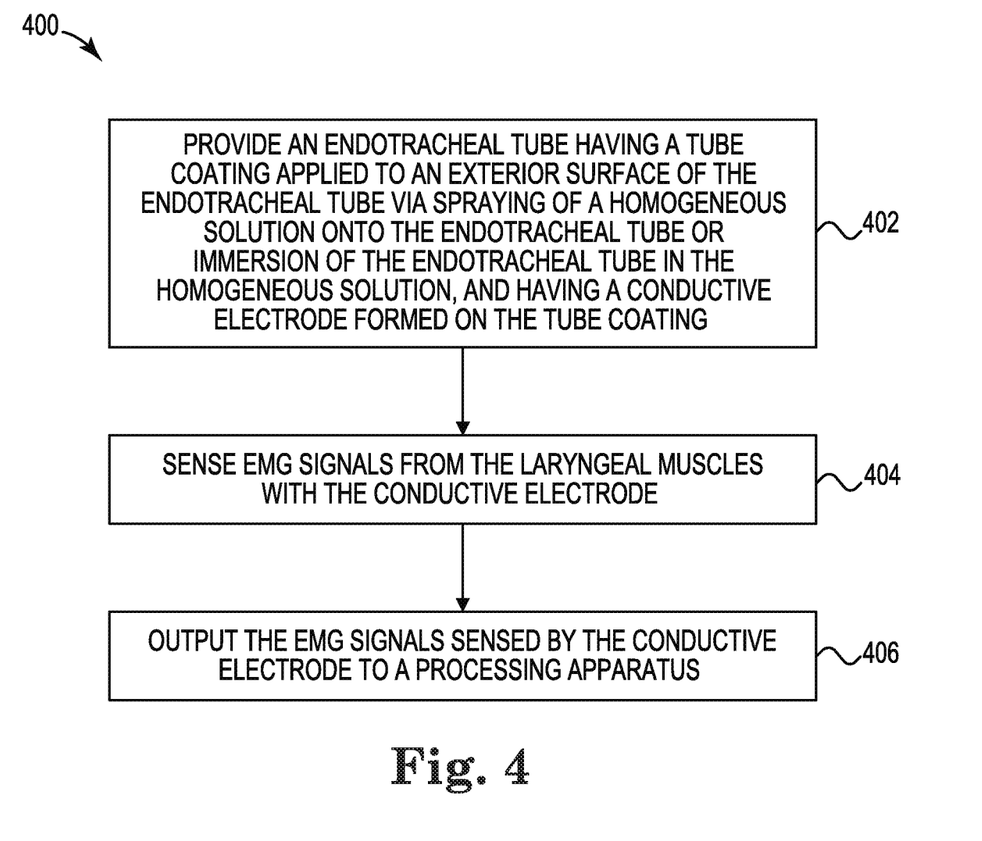
FIG. 4 is a flow diagram illustrating a method of monitoring EMG signals of a patient's laryngeal muscles according to one embodiment.

Another embodiment is directed to a method of monitoring EMG signals. FIG. 4 is a flow diagram illustrating a method 400 of monitoring EMG signals of a patient's laryngeal muscles according to one embodiment. At 402 in method 400, an endotracheal tube having a tube coating applied to an exterior surface of the endotracheal tube via spraying of a homogeneous solution onto the endotracheal tube or immersion of the endotracheal tube in the homogeneous solution, and having a conductive electrode formed on the tube coating, is provided. At 404, the EMG signals from the laryngeal muscles are sensed with the conductive electrode. At 406, the EMG signals sensed by the conductive electrode are output to a processing apparatus.

The tube coating in method 400 may cause the endotracheal tube to have a color tint, and the tube coating may have a transmittance of about 74-93%. The tube coating may be formed from spraying the homogeneous solution in an aerosol form onto the endotracheal tube. The tube coating may be formed from a PVC solute dissolved in a mixture of solvents to form the homogeneous solution. The mixture of solvents may include cyclohexanone, tetrahydrofuran (THF), acetone, and an ink thinner. The homogeneous solution may include a food grade colorant.

Figure 5:
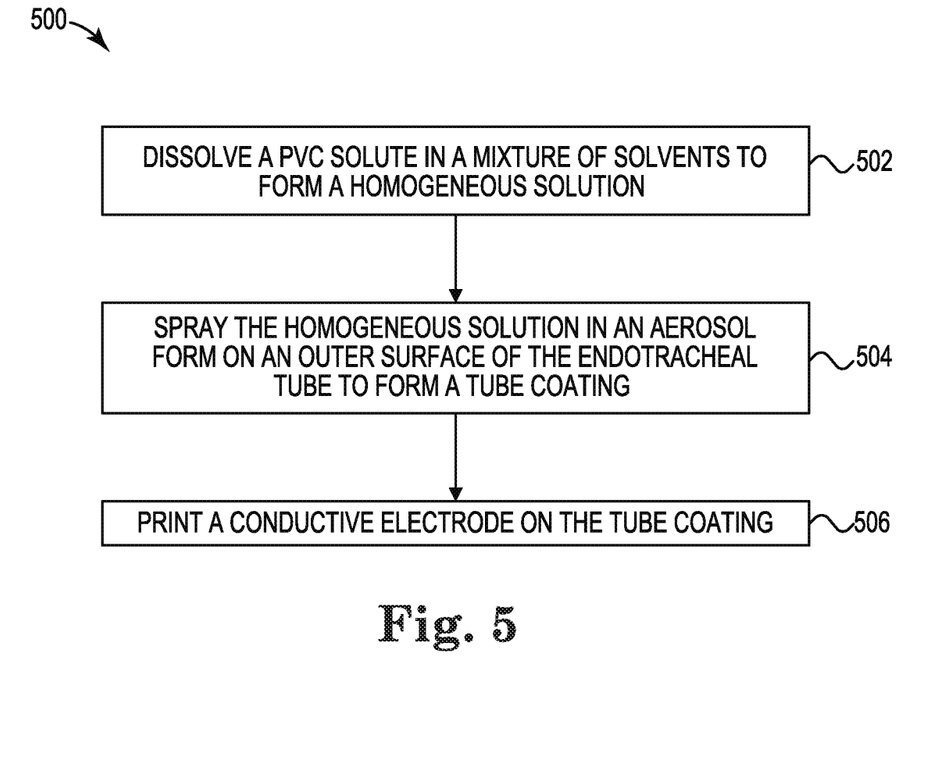
FIG. 5 is a flow diagram illustrating a method of applying an electrode to an endotracheal tube according to one embodiment.

Yet another embodiment is directed to a method of applying an electrode to an endotracheal tube. FIG. 5 is a flow diagram illustrating a method 500 of applying an electrode to an endotracheal tube according to one embodiment. At 502 in method 500, a PVC solute is dissolved in a mixture of solvents to form a homogeneous solution. At 504, the homogeneous solution is sprayed in an aerosol form on an outer surface of the endotracheal tube to form a tube coating. At 506, a conductive electrode is printed on the tube coating.

The method 500 may further include adding a food grade colorant to the homogeneous solution before the spraying of the homogeneous solution. The method 500 may further include masking at least one region of the endotracheal tube before the spraying of the homogeneous solution to prevent formation of the tube coating in the at least one masked region. The method 500 may further include stirring the PVC solute and the mixture of solvents with a magnetic stirrer. The method 500 may further include rotating the endotracheal tube during the spraying of the homogeneous solution.

Although the present disclosure has been described with reference to preferred embodiments, workers skilled in the art will recognize that changes can be made in form and detail without departing from the spirit and scope of the present disclosure.

What is claimed is:

1. An apparatus for monitoring EMG signals of a patient's laryngeal muscles, comprising:
    an endotracheal tube having an exterior surface;
    a tube coating applied to the exterior surface via spraying of a homogeneous solution onto the endotracheal tube or immersion of the endotracheal tube in the homogeneous solution; and
    a conductive electrode formed on the tube coating that has been applied to the exterior surface, the conductive electrode configured to receive the EMG signals from the laryngeal muscles.

2. The apparatus of claim 1, wherein the tube coating causes the endotracheal tube to have a color tint.

3. The apparatus of claim 2, wherein the tube coating has a transmittance of 74-93%.

4. The apparatus of claim 1, wherein the tube coating is applied only to an electrode region of the endotracheal tube.

5. The apparatus of claim 1, wherein the tube coating is formed from spraying the homogeneous solution in an aerosol form onto the endotracheal tube.

6. The apparatus of claim 1, wherein the tube coating is formed from PVC pellets dissolved in a mixture of solvents to form the homogeneous solution.

7. The apparatus of claim 6, wherein the mixture of solvents includes cyclohexanone, tetrahydrofuran (THF), and acetone.

8. The apparatus of claim 7, wherein the mixture of solvents further includes an ink thinner.

9. The apparatus of claim 6, wherein the homogeneous solution includes a food grade colorant.

10. A method of monitoring EMG signals of a patient's laryngeal muscles, comprising:
    providing an endotracheal tube having a tube coating applied to an exterior surface of the endotracheal tube via spraying of a homogeneous solution onto the endotracheal tube or immersion of the endotracheal tube in the homogeneous solution, and having a conductive electrode formed on the tube coating that has been applied to the exterior surface;
    sensing the EMG signals from the laryngeal muscles with the conductive electrode; and outputting the EMG signals sensed by the conductive electrode to a processing apparatus.

11. The method of claim 10, wherein the tube coating causes the endotracheal tube to have a color tint, and wherein the tube coating has a transmittance of 74-93%.

12. The method of claim 10, wherein the tube coating is formed from spraying the homogeneous solution in an aerosol form onto the endotracheal tube.

13. The method of claim 10, wherein the tube coating is formed from a PVC solute dissolved in a mixture of solvents to form the homogeneous solution.

14. The method of claim 13, wherein the mixture of solvents includes cyclohexanone, tetrahydrofuran (THF), acetone, and an ink thinner.

15. The method of claim 13, wherein the homogeneous solution includes a food grade colorant.

16. A method of applying an electrode to an endotracheal tube, comprising:
dissolving a PVC solute in a mixture of solvents to form a homogeneous solution;
spraying the homogeneous solution in an aerosol form on an outer surface of the endotracheal tube to form a tube coating; and
printing a conductive electrode on the tube coating.

17. The method of claim 16, and further comprising:
adding a food grade colorant to the homogeneous solution before the spraying of the homogeneous solution.

18. The method of claim 16, and further comprising:
masking at least one region of the endotracheal tube before the spraying of the homogeneous solution to prevent formation of the tube coating in the at least one masked region.

19. The method of claim 16, and further comprising:
stirring the PVC solute and the mixture of solvents with a magnetic stirrer.

20. The method of claim 16, and further comprising:
rotating the endotracheal tube during the spraying of the homogeneous solution.

\* \* \* \* \*